US012762657B2

(12) United States Patent
Ren

(10) Patent No.: US 12,762,657 B2

(45) Date of Patent: Oct. 13, 2026

(54) TOMOSYNTHESIS GAIN CALIBRATION AND IMAGE CORRECTION

(71) Applicant: Hologic, Inc., Marlborough, MA (US)

(72) Inventor: Baorui Ren, Andover, MA (US)

(73) Assignee: Hologic, Inc., Marlborough, MA (US)

(*) Notice: Subject to any disclaimer, the term of this patent is extended or adjusted under 35 U.S.C. 154(b) by 52 days.

(21) Appl. No.: 18/928,531

(22) Filed: Oct. 28, 2024

(65) Prior Publication Data

US 2025/0157001 A1 May 15, 2025

Related U.S. Application Data

(63) Continuation of application No. 18/692,989, filed as application No. PCT/US2022/076831 on Sep. 22, 2022, now Pat. No. 12,159,375.

(60) Provisional application No. 63/247,503, filed on Sep. 23, 2021.

(51) Int. Cl.

| | |
|---|---|
| ***A61B 6/00*** | (2024.01) |
| ***A61B 6/02*** | (2006.01) |
| ***A61B 6/50*** | (2024.01) |
| ***A61B 6/58*** | (2024.01) |
| ***G06T 5/50*** | (2006.01) |

(52) U.S. Cl.

CPC ................ *G06T 5/50* (2013.01); *A61B 6/025* (2013.01); *A61B 6/502* (2013.01); *A61B 6/582* (2013.01); *G06T 2207/10116* (2013.01); *G06T 2207/20016* (2013.01); *G06T 2207/20216* (2013.01); *G06T 2207/30068* (2013.01)

(58) Field of Classification Search

CPC ...................................................... A61B 6/025

See application file for complete search history.

(56) References Cited

U.S. PATENT DOCUMENTS

| | | | |
|---|---|---|---|
| 5,625,662 A | 4/1997 | Toth | |
| 9,851,460 B1 | 12/2017 | Rodrigues et al. | |
| 2007/0003006 A1 | 1/2007 | Tkaczyk et al. | |
| 2008/0093545 A1 * | 4/2008 | Manak .................. | A61B 6/585 250/252.1 |
| 2012/0328176 A1 | 12/2012 | Ren et al. | |
| 2016/0206264 A1 | 7/2016 | Fukuda et al. | |
| 2018/0292544 A1 | 10/2018 | Persson | |

(Continued)

FOREIGN PATENT DOCUMENTS

| | | |
|---|---|---|
| JP | 2009-171990 A | 8/2009 |
| JP | 2016-156748 | 9/2016 |

(Continued)

OTHER PUBLICATIONS

Geiser, William et al., "Artifacts in Digital Breast Tomosynthesis", AJR:211, Oct. 2018, p. 926-962.

(Continued)

*Primary Examiner* — Dani Fox

(74) *Attorney, Agent, or Firm* — Merchant & Gould P.C.

(57) ABSTRACT

The present application discloses a tomosynthesis system and method that combines high dose gain maps directly, or high-resolution components of high dose gain maps, with low resolution components of low dose gain maps at a plurality of imaging parameters, to produce high quality gain map efficiently at the plurality of imaging parameters, to perform gain corrections to x-ray images.

20 Claims, 9 Drawing Sheets

(56) References Cited

U.S. PATENT DOCUMENTS

| | | | |
|---|---|---|---|
| 2020/0036266 A1 | 1/2020 | Uematsu et al. |
| 2020/0060636 A1 | 2/2020 | Wilson et al. |
| 2020/0069266 A1 | 3/2020 | Cai |
| 2023/0358904 A1 | 11/2023 | Kelly |
| 2024/0331101 A1 | 10/2024 | Ren |

FOREIGN PATENT DOCUMENTS

| | | |
|---|---|---|
| WO | 2010/070583 | 6/2010 |
| WO | 2013/144812 | 10/2013 |

OTHER PUBLICATIONS

Katsuyuki Taguchi et al., "An analytical model of the effects of pulse pileup on the energy spectrum recorded by energy resolved photon counting x-ray detectors", Med. Phys. 37(8): 3957-3969 (2010).

PCT International Preliminary Report on Patentability in Application PCT/US2022/076831, mailed Apr. 4, 2024, 6 pages.

PCT International Search Report and Written Opinion in Application PCT/US2022/076831, mailed Dec. 9, 2022, 13 pages.

Yew Samantha et al., "Digital tomosynthesis: Applications in general radiography", Radiology Open Journal 2020; 4(1): 23-29.

* cited by examiner

TOMOSYNTHESIS GAIN CALIBRATION AND IMAGE CORRECTION

CROSS-REFERENCE TO RELATED APPLICATION

This application is a continuation of U.S. patent application Ser. No. 18/692,989, filed Mar. 18, 2024, now U.S. Pat. No. 12,159,375, which is a National Stage Application of PCT/US2022/076831, filed Sep. 22, 2022, which claims priority to and the benefit of U.S. Provisional Application No. 63/247,503, filed on Sep. 23, 2021, the entire disclosures of which are incorporated herein by reference in their entireties.

BACKGROUND

Breast cancer and other breast lesions continue to be a significant threat to women's health. X-ray mammography and breast tomosynthesis are the most widely used tools for early detection, screening, and diagnosis. Breast tomosynthesis is a technique that allows physicians to view multiple images of the breast rather than a single image available from a conventional mammogram.

For example, convention mammography provides physicians with a single two-dimensional (2D) image to evaluate the breast. However, this can be limiting due to the overlapping layers of tissue, which can produce unclear results, false alarms or can lead the physician to miss cancerous growth. By contrast, instead of taking an image of the breast from top to bottom and side to side as conventional mammography does, digital breast tomosynthesis follows the curvature of the breast and takes several images of the breast as it moves. The images are then compiled into a sharp, clear, three-dimensional (3D) image that allows physicians to better evaluate the patient's breast.

SUMMARY

Embodiments of the disclosure are directed to a tomosynthesis methods and systems for gain calibration and correction of breast images in association with breast tomosynthesis methods.

In a first aspect, a method for gain calibration at a plurality of imaging parameters for a tomosynthesis sweep is disclosed. The method includes: performing one or more tomosynthesis sweeps to acquire a plurality of tomosynthesis projection x-ray images, each of the plurality of tomosynthesis projection x-ray images associated with one of the plurality of imaging parameters; generating a high-dose x-ray image by averaging the plurality of tomosynthesis projection x-ray images; generating a high-dose gain map associated with the high-dose x-ray image; generating a plurality of low-dose gain maps, each of the plurality of low-dose gain maps associated with one of the plurality of tomosynthesis projection x-ray images associated with one of the plurality of imaging parameters; decomposing each of the plurality of low-dose gain maps into a plurality of component levels; extracting low-resolution components from the plurality of component levels for each of the plurality of low-dose gain maps; and for each of the plurality of imaging parameters, combining the high-dose gain map with the each of the low-resolution components of the low-dose gain maps to generate a final gain map for each of the plurality of imaging parameters.

In a second aspect, a tomosynthesis system for gain calibration at a plurality of projection angles is disclosed. The system includes: an image acquisition unit comprising an x-ray source and an x-ray image receptor, wherein the image acquisition unit acquires projection x-ray images of an object at the plurality of projection angles; a processor; memory including instructions that when executed by the processor cause the processor to: perform one or more tomosynthesis sweeps to acquire a plurality of tomosynthesis projection x-ray images, each of the plurality of tomosynthesis projection x-ray images associated with one of the plurality of projection angles; generate a high-dose x-ray image by averaging the plurality of tomosynthesis projection x-ray images; generate a high-dose gain map associated with the high-dose x-ray image; decompose the high-dose gain map into a first plurality of component levels; extract a high-resolution component from the first plurality of component levels; generate a plurality of low-dose gain maps, each of the plurality of low-dose gain maps associated with one of the plurality of tomosynthesis projection x-ray images associated with one of the plurality of projection angles; decompose each of the plurality of low-dose gain maps into a second plurality of component levels; extract low-resolution components from each of the plurality of low-dose gain maps, wherein the low-resolution components comprise an angle map; and for each of the plurality of projection angles, combine the high-resolution component of the high-dose gain map with the each of the low-resolution components of the low-dose gain maps to generate a final gain map for each of the plurality of projection angles.

In a third aspect, a method for gain calibration at a plurality of projection angles for a tomosynthesis sweep is disclosed. The method includes: performing one or more tomosynthesis sweeps to acquire a plurality of tomosynthesis projection x-ray images, each of the plurality of tomosynthesis projection x-ray images associated with one of the plurality of projection angles; generating a high-dose x-ray image by averaging the plurality of tomosynthesis projection x-ray images; generating a high-dose gain map associated with the high-dose x-ray image; decomposing the high-dose gain map into a first plurality of component levels; extracting a high-resolution component from the first plurality of component levels; generating a plurality of low-dose gain maps, each of the plurality of low-dose gain maps associated with one of the plurality of tomosynthesis projection x-ray images associated with one of the plurality of projection angles; decomposing each of the plurality of low-dose gain maps into a second plurality of component levels; extracting low-resolution components from each of the plurality of low-dose gain maps, wherein the low-resolution components comprise an angle map; and for each of the plurality of projection angles, combining the high-resolution component with the each of the low-resolution components to generate a final gain map for each of the plurality of projection angles.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description. Embodiments of the present disclosure will hereinafter be described in conjunction with the appended drawings, wherein like numerals denote like elements.

DETAILED DESCRIPTION

Figure 1A:
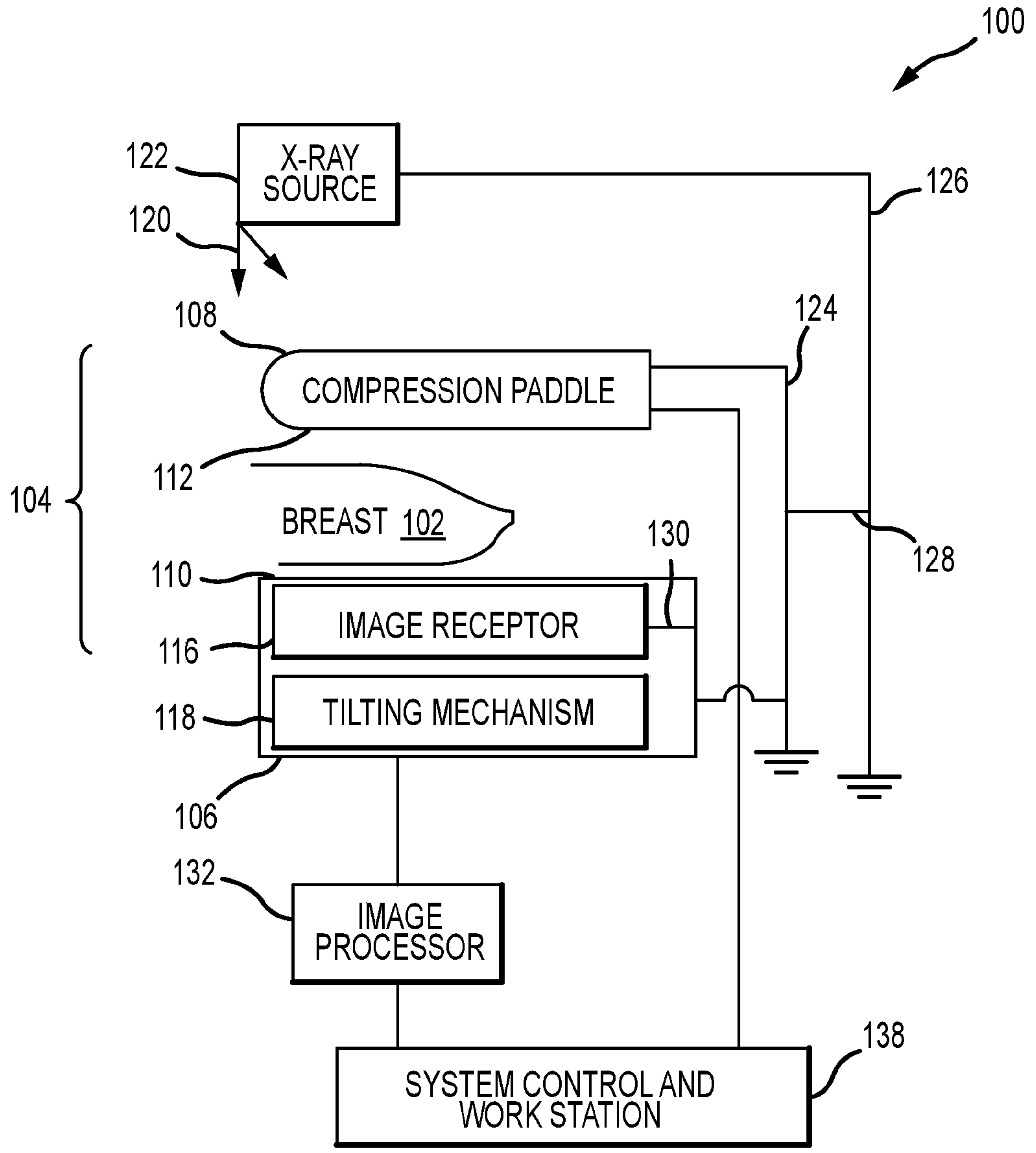
FIG. 1A is a schematic view of an exemplary imaging system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Digital tomosynthesis is a “three-dimensional” process in which several two-dimensional projection views are acquired at respective different angles but at lower x-ray dose each compared to a conventional mammogram, and are reconstructed into tomosynthesis slice views that can be along any desired plane in the breast and can represent any thickness of breast tissue. Thus, the combined reconstructed tomosynthesis image set represents the entire thickness of the breast, in a stack of two-dimensional images. For tomosynthesis, the breast is immobilized or compressed to the same or lesser extent than in conventional mammography.

When digital flat panel x-ray imaging receptors are used in acquiring tomosynthesis images, one of the practical requirements is to provide gain calibration. The imaging receptor may comprise a two-dimensional array of millions of imaging pixels, and there may be inherent differences in the response of different imaging pixels to impinging x-rays. When all imaging pixels receive the same x-ray exposure, ideally each should provide the same electrical output signal (pixel value).

However, in practice this may not be the case and typically there are differences between the pixel values that different imaging pixels provide when exposed to the same x-ray input. In addition, incident x-ray intensity across the detector surface usually is non-uniform; for example, due to the “heel effect” the x-ray intensity drops along the direction from the chest wall to the nipple. To correct for differences in pixel values in response to uniform x-ray exposure, and to correct for the non-uniform x-ray intensity distribution across the x-ray imaging detector surface area, various gain calibration and image correction techniques are employed.

Typically, in the testing or servicing of a conventional x-ray mammography system, the flat panel imager is exposed to an x-ray field through a phantom that simulates a patient’s breast and has a generally uniform thickness and is made of a uniform material, the differences between pixel values are recorded, and a gain correction map is generated that accounts for such differences. This can be done periodically during the service life of the flat panel x-ray receptor. The gain map is stored in the imaging system and, when x-ray images of a patient’s breast are taken during actual imaging procedures, software in the system corrects the acquired pixel values according to the gain map to bring them closer to the pixel values that would have been produced if all the imaging pixels had the same response to uniform exposure to x-ray energy.

For conventional mammography, usually one gain map is acquired for each viewing mode or x-ray filter mode. Gain calibration thus can be used to compensate for sensitivity differences between detector pixels and non-uniform x-ray field intensity given a particular physical relationship between the x-ray source and imaging detector.

However, tomosynthesis imaging is characterized by a much greater number of changes in x-ray source projection angle during x-ray exposure, much lower x-ray exposure of the breast at any one of the projection angles, and other significant differences from conventional mammography imaging. As a result, gain maps typical for conventional mammography cannot be expected to work well in tomosynthesis image acquisition and image correction, particularly if the tomosynthesis projection angles may change depending on imaging protocol or decisions or preferences of the health professional (e.g., an imaging technologist) in charge.

One solution for gain correcting images obtained during the tomosynthesis process includes obtaining gain map images at each view angle in order to make gain-corrected images flat at all angles. However, tomosynthesis methods may include obtaining images at 15 or sometimes even 60 individual angles. In such a case, a gain map for each of these angles is required in order to perform the appropriate gain correction. Each gain map requires high x-ray dose exposures to maintain good photon statistics to reduce image noise, which makes gain calibration a very high tube loading procedure. Therefore, there is a need for a better and more efficient gain mapping method.

Gain mapping consists of contributions from different sources in a system, e.g., detector pixel to pixel variation effect, tube heel effect, view angle effect, filter, anti-scatter grid, kilovoltage peak (KVp), phantom thickness, etc. Among the different components of a final gain map, the detector pixel-to-pixel variations are the most dose-demanding task and require high-dose exposures to reliably measure them. Other components of the final gain map carry low frequency information and do not require high dose exposures for measurements.

A multi-scale decomposition can be performed to analyze gain maps at different scales and layers. For example, a gain map may be the product of high-resolution and low-resolution component maps.

Typically, the high-resolution detailed images can look flat and may not contain any information on image tilt related to factors like the heel effect and view angle effect. The high-resolution layers may mainly contain detector pixel-to-pixel variation information. On the other hand, low-resolution residue images may clearly show heel effect, view angle effect and other low frequency factors. The low-resolution residue images may be obtained using low dose exposures. The low-resolution layers may contain tube heel effect, view angle effect, filter effect, anti-scatter grid effect, KVp effect, and phantom thickness effect.

The component maps of a tomosynthesis gain map at two different angles may typically look identical except for the angle map. In other words, the components maps associated with the detector pixel-to-pixel variation, tube heel effect, filter, anti-scatter grid, KVp, and phantom thickness effects are almost identical at different angles. The main difference between tomosynthesis gain maps at two different angles is the angle map.

The disclosed system and method may combine all components other than the angle map together and treat it as a common reference map. The common reference map may then be combined with each angle map associated with each of the angles of the tomosynthesis process. Thus, the disclosed system and method helps avoid high x-ray dose exposures at each view angle while still maintaining good photon statistics to reduce image noise.

Figure 1B:
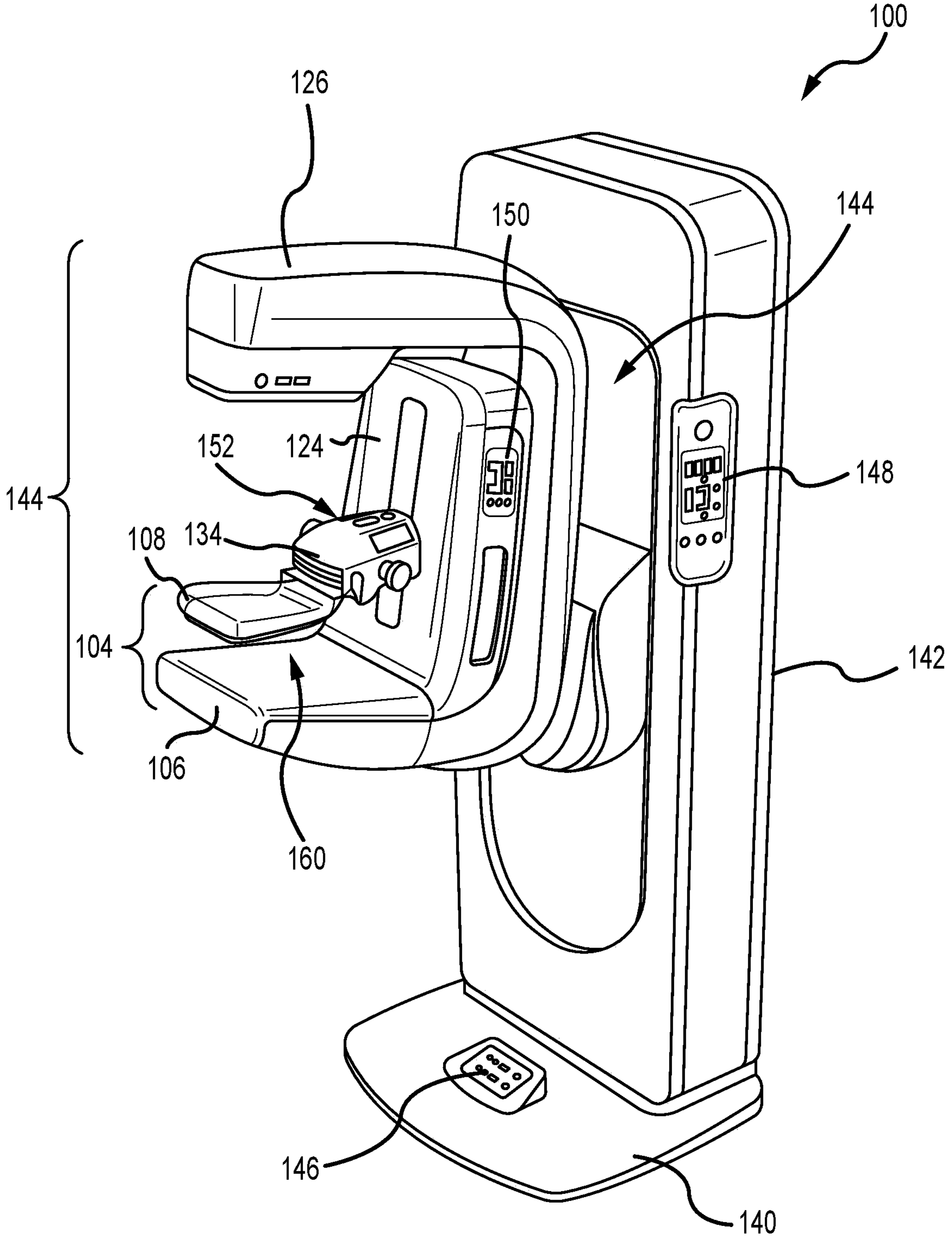
FIG. 1B is a perspective view of the imaging system of FIG. 1A.

FIG. 1A is a schematic view of an exemplary imaging system 100 and FIG. 1B is a perspective view of the imaging system 100. Referring concurrently to FIGS. 1A and 1B, not every element described below is depicted in both figures. The imaging system 100 immobilizes a patient's breast 102 for x-ray imaging (either or both of mammography, tomosynthesis, or other imaging modalities) via a breast compression immobilizer unit 104 that includes a static breast support platform 106 and a moveable paddle 108. Different paddles, each having different purposes, are known in the art. Certain examples paddles are also described herein for context. The breast support platform 106 and the paddle 108 each have a compression surface 110 and 112, respectively, that move towards each other to compress, immobilize, stabilize, or otherwise hold and secure the breast 102 during imaging procedures. In known systems, the compression surface 110, 112 is exposed so as to directly contact the breast 102. Either or both of these compression surfaces 110, 112 may be rigid plastic, a flexible plastic, a resilient foam, a mesh or screen, and so on. The platform 106 also houses an image receptor 116 and, optionally, a tilting mechanism 118, and optionally an anti-scatter grid (not depicted, but disposed above the image receptor 116). The immobilizer unit 104 is in a path of an imaging beam 120 emanating from x-ray source 122, such that the beam 120 impinges on the image receptor 116.

The immobilizer unit 104 is supported on a first support arm 124 via a compression arm 134, which is configured to be raised and lowered along the support arm 124. The x-ray source 122 is supported on a second support arm, also referred to as a tube head 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, other modalities such as ultrasound, or a "combo" system that can perform multiple forms of imaging. An example of a system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images.

A system control and work station unit 138 including software controls the operation of the system and interacts with the operator to receive commands and deliver information including processed-ray images. The system control and work station unit 138 may include an image correction engine that may be configured to generate gain correction maps and gain correct breast x-ray images based on the generated gain correction maps. The configuration of the image correction engine is described in greater detail in relation to FIG. 2.

The imaging system 100 includes a floor mount or base 140 for supporting the imaging system 100 on a floor. A gantry 142 extends upwards from the floor mount 140 and rotatably supports both the tube head 208 and a support arm 210. The tube head 126 and support arm 124 are configured to rotate discretely from each other and may also be raised and lowered along a face 144 of the gantry 142 so as to accommodate patients of different heights. The x-ray source 122 is disposed within the tube head 208. Together, the tube head 126 and support arm 124 may be referred to as a C-arm 144.

A number of interfaces and display screens are disposed on the imaging system 100. These include a foot display screen 146, a gantry interface 148, a support arm interface 150, and a compression arm interface 152. In general the various interfaces 148, 150, and 152 may include one or more tactile buttons, knobs, switches, as well as one or more display screens, including capacitive touch screens with graphic user interfaces (GUIs) so as to enable user interaction with and control of the imaging system 100. In general, the foot display screen 146 is primarily a display screen, though a capacitive touch screen might be utilized if required or desired.

Figure 2:
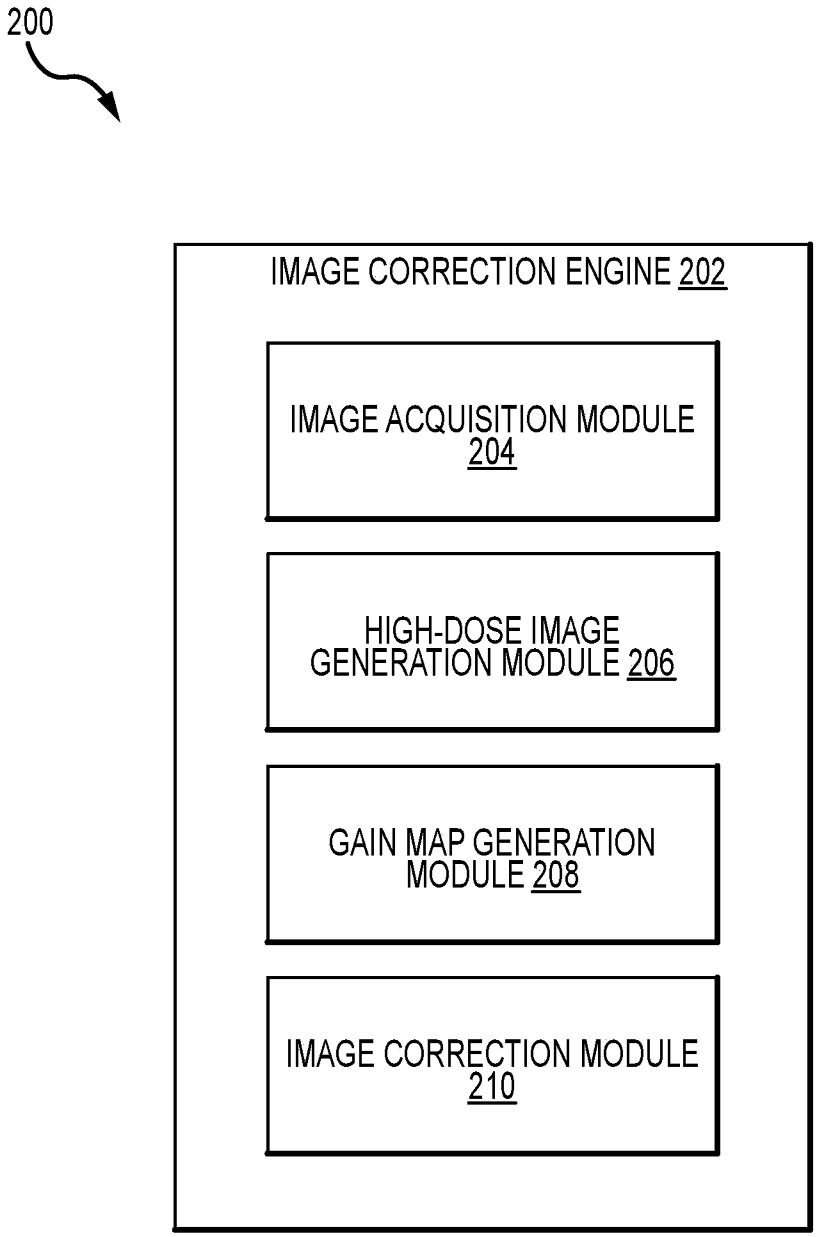
FIG. 2 illustrates an example configuration of an image correction engine of the system of FIG. 1A.

FIG. 2 illustrates an example configuration 200 of an image correction engine 202 of the system of FIG. 1A. For example, the image correction engine 202 may be configured within the workstation 138 of the imaging system 100. As such, the description of FIG. 2 refers to components depicted in FIGS. 1A and 1B and are numbered accordingly. The image correction engine 202 may be configured to include an image acquisition module 204, a high-dose image generation module 206 and a gain map generation module 208. Other types of modules are also possible.

The image acquisition module 204 may be configured to cause the imaging system 100 to acquire x-ray images of a phantom or a patient's breast at a plurality of imaging parameters as required for a tomosynthesis process. Although the example configuration 200 is largely described in association with gain calibration at imaging parameters that primarily includes the projection angle, other types of imaging parameters can also be used in the methods for gain calibration. For example, the imaging parameter can be one of: kVp, filter material type, breast thickness, and grid position. Other types of imaging parameters are also possible.

The image acquisition module 204 may cause the imaging system 100 to perform tomosynthesis data acquisition at a plurality of projection angles. In some systems 100, the image receptor 116 may move relative to the immobilizer unit 104 during tomosynthesis data acquisition. In other systems, the image receptor 115 may move differently or not at all. Typically, the motion may be motorized. The motion of the x-ray source 122 can be continuous or the x-ray source can stop and emit imaging x-rays at one projection angle before moving to another projection angle. Image receptor 116 may provide projection image data in the form of an array of pixel values related to incident x-ray energy.

In the case of a calibration sequence, a calibration phantom can be secured in the immobilizer unit 104, in a position similar to that of a patient's breast when x-rays of a patient's breast are taken. The image acquisition module 204 may then cause the imaging system to perform the tomosynthesis data acquisition associated with the phantom at a plurality of projection angles.

To acquire projection images of the patient the patient's breast may be secured in the immobilizer unit 104. The image acquisition module 204 may then cause the imaging system 100 to perform the tomosynthesis data acquisition associated with the patient's breast at a plurality of projection angles.

The high-dose image generation module 206 may be configured to generate a high-dose x-ray image from the plurality of tomosynthesis x-ray projection images of the phantom that were acquired by the image acquisition module 204 at the plurality of projection angles. The generated high-dose x-ray image may be used by the gain map generation module 208 in generating a gain correction map.

In a non-limiting example, the imaging system 100 may be configured to perform the tomosynthesis imaging of a phantom at 15 projection angles. The imaging system 100 performing the tomosynthesis imaging will generate 15 x-ray images of the phantom. However, each of the 15 images may appear "noisy" since the number of photons per pixel is relatively low due to the low-dose nature of the scans. For example, in a "three-dimensional" tomosynthesis scan using 32 kV, 120 mAs at 15 projections, the x-ray exposure for each view is 8 mAs and the photon number for each pixel in a detector pixel array of 0.07 mm×0.07 mm may only be about 2000 photons. This may cause the resulting x-ray images to appear noisy. The resulting gain map from the noisy images may include errors due to the low photon numbers.

One solution to the above described problem related to noisy images may be solved by repeating the scans several times. If the tomosynthesis scans using 32 kV and 120 mAs were repeated 5 times and a three-neighbor view average were to be used, the photon number for each pixel in the gain map at each view angle may be 30 k photons (2000×3×5). However, such a solution would require 5 tomosynthesis scans, which takes a considerable amount of time and negatively impacts the life of the x-ray tube.

The disclosed high-dose image generation module 206 provides a solution for acquiring a high-dose image using only one tomosynthesis scan by using all the low-dose images together to create a new high-dose image. The high-dose image generation module 206 may combine and average images from each of the projection angles of a single tomosynthesis scan to create a high-dose image that does not include the noise seen in the low-dose images.

For a tomosynthesis scan that includes 15 projection angles, where the photon number per pixel per angle is 2000, a new high-dose image may be created by combining and averaging the 15 images. The newly created high-dose image would have a photon number per pixel of 30 k photons (2000×15). Thus, the high-dose image generation module 206 may produce a high-dose image that can be used to generate a gain map that minimizes noise caused due to the low photon count.

The Gain map generation module 208 is configured to create a gain correction map that may be used to gain correct patient breast images. For example, the plurality of x-ray projection images of the phantom acquired by the image acquisition module 204 and the associated high-dose image generated by the high-dose image generation module 206 may be used to generate a gain correction map.

Although a high-dose gain map derived from the high-dose image generated by combining the plurality of low-dose images acquired at the plurality of projection angles by the high-dose image generation module 206 may be less noisy, any gain corrections made using the high-dose gain map may look tilted or cupped. In other words, any image that is gain corrected by the high-dose gain map may not look flat since the high-dose gain map does not include the corrected angle information.

Although each of the low-dose gain maps derived from the low-dose images, each acquired at each of the plurality of projection angles by the image acquisition module 204, may look flat due to the correct and accurate angle information, any gain corrections made using the low-dose gain maps may look noisy due to the low photon count of the image.

Using a combination of the high-dose gain map and low-dose gain maps to generate a final gain map may result in gain corrected image that is both less noisy as well as flat. In an example, the gain map generation module 208 may be configured to generate a low-dose gain map from each of the low-dose images corresponding to each of the projection angles of the tomosynthesis scan. In another example, the gain map generation module 208 may be configured to generate a high-dose gain map from the high-dose image that was generated by combining the plurality of low-dose images, as described above in relation to the high-dose image generation module 206. The final gain map may then be generated by combining components from the high-dose gain map with components from the low-dose gain maps.

Figure 3:
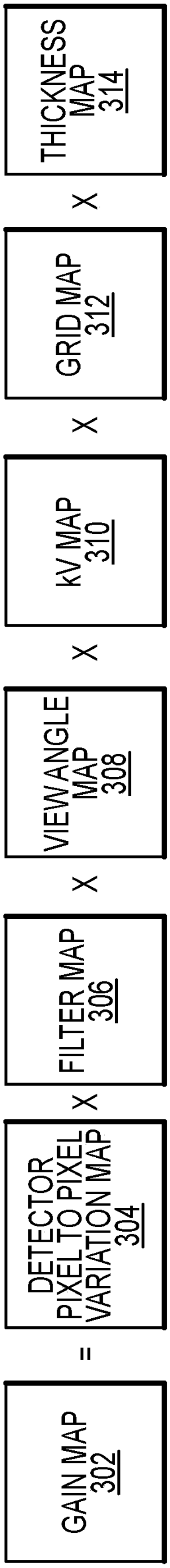
FIG. 3 illustrates an example schematic representation of the components of a gain map. In some examples, a gain map consists of contributions from different sources in a system.
Figure 4:
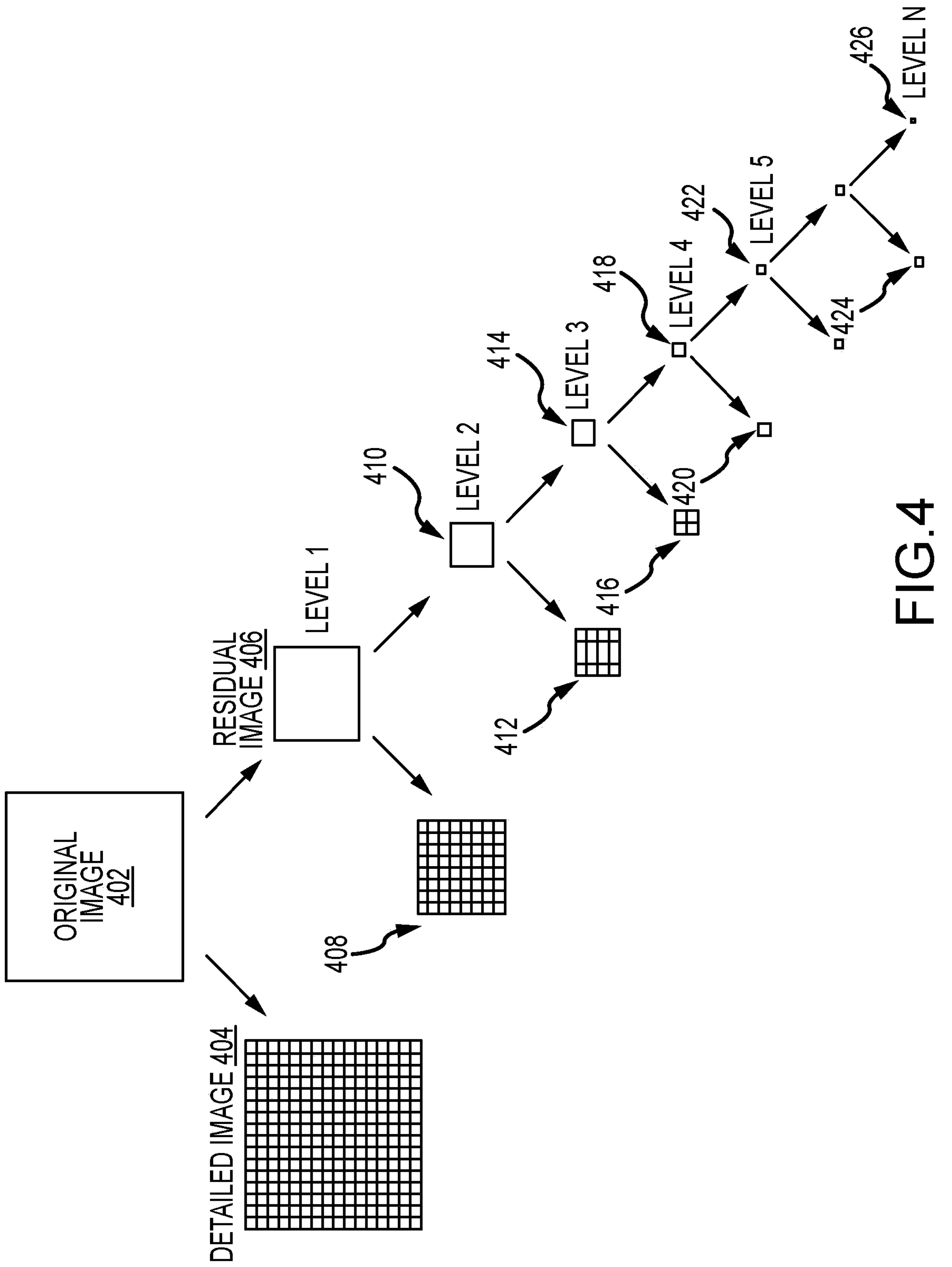
FIG. 4 illustrates an example schematic representation of decomposition of a gain map into multi-scale components.
Figure 5:
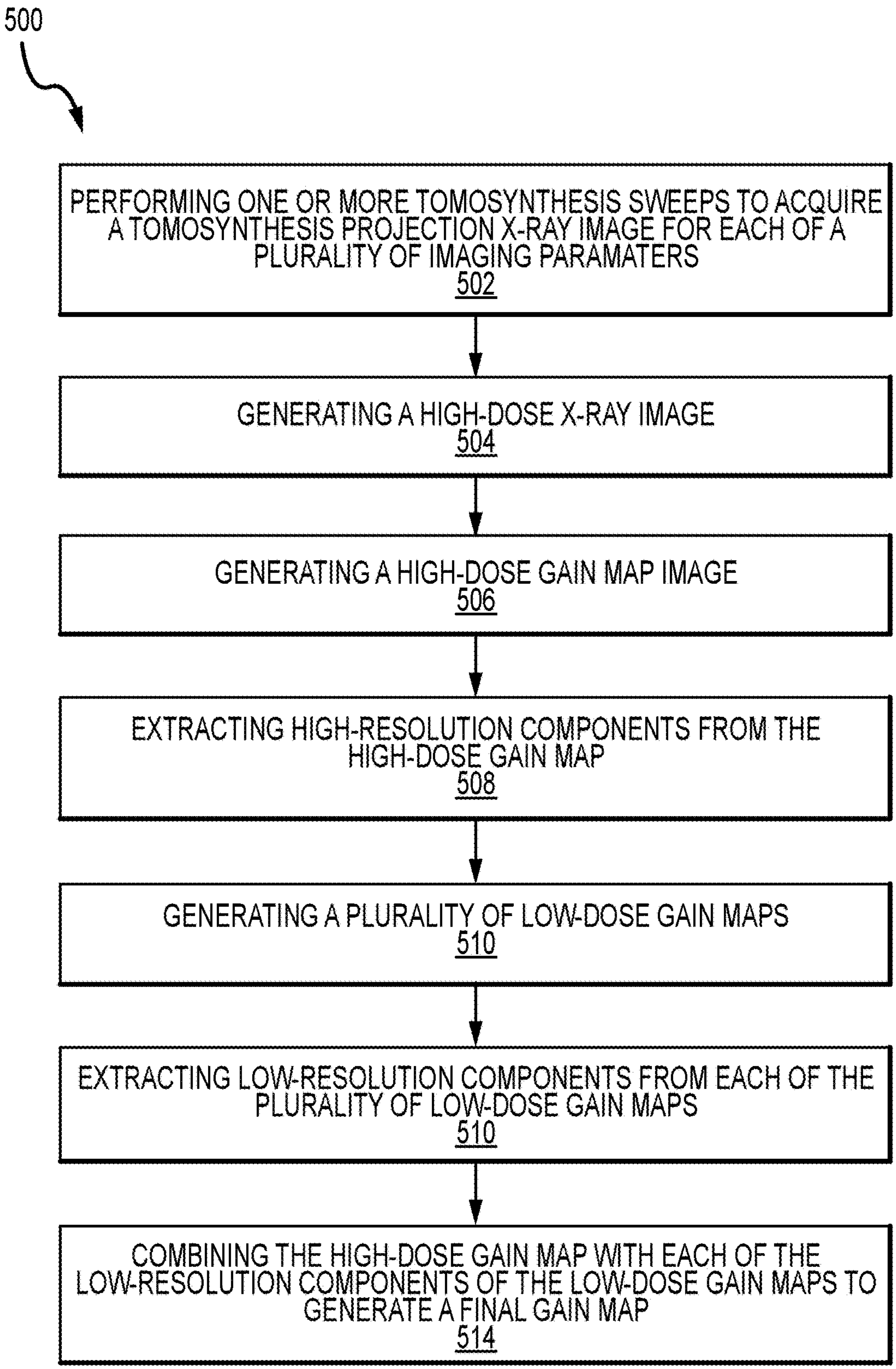
FIG. 5 illustrates an example method for gain calibration at a plurality of projection angles for a tomosynthesis sweep.

The process of decomposing the high-dose gain map and low-dose gain maps into component levels and combining the high-resolution component of the high-dose gain map with the low resolution components of the plurality of low-dose gain maps is described in further detail in relation to FIGS. 3-5.

The image correction module 210 may be configured to receive the x-ray images of a patient's breast at each of the plurality of projection angles from the image acquisition module 204 and gain correct the received x-ray images of the patient's breast using the final gain map from the gain map generation module 208.

To acquire projection images of the patient, the phantom is removed and a patient's breast is secured to the immobilizer unit 104. The image acquisition module 204 is then configured to x-ray the patient's breast using tomosynthesis imaging sequences. For example, the tomosynthesis imaging sequence of a patient's breast generates projection x-ray images taken at a plurality of projection angles.

The image correction module 210 receives the projection x-ray images of the patient's breast taken at a plurality of projection angles and final gain map from the gain map generation module 208. For each of the projection angles, the image correction module 210 may then use the final gain map to make adjustments to the gain values associated with each pixel of the projection x-ray images to create a gain-corrected set of projection x-ray images. FIG. 3 illustrates an example schematic representation of the components of a gain map.

A gain map consists of contributions from different sources in a system. For example, gain map 302 may be a product of individual components including detector pixel-to-pixel variation map 304, filter map 306, view angle map 308, kV map 310, grid map 312 and thickness map 314. In other examples, gain map 302 may be a product of more, fewer or different individual components.

A detector map may contain only the detector's pixel-to-pixel gain variations. When x-ray beams with spatially uniform intensity irradiate flat panel x-ray detector, the raw x-ray image may not look uniform in signal counts among all pixels. Since the x-ray to electrical signal conversion power are not exactly same among different pixels, each pixel generates electrical signals that may be different to other pixels in the detector. In other words, the detector gain at each pixel may be different. For example, the map of the inverse of detector gain at each pixel may be referred as detector gain map, or detector map. When the detector map is multiplied to the raw image, the signal counts in the new image may become identical and detector pixel-to-pixel gain variations are all cancelled out.

The beam intensity from x-ray tube may not have uniform spatial distribution on detector surface, which is referred as heel effect. The heel effect may be affected by a few factors, including, kVp, filter, thickness, and grid. The factors that affect the heel effect ultimately also affect the system gain map. Ideally, a perfect gain map compensates for the heel effects contributed by the factors including but not limited to, kVp, filter, thickness, and grid. Therefore, a gain map may include components related to each of these factors, and the gain map can be decomposed into a product of components that related to each of these factors.

For example, x-ray filter of different materials and thicknesses can modify the x-ray signal profile differently. A system gain map measured with a 0.05 mm thick rhodium filter may be different from the gain map measured with a 0.7 mm aluminum filter. X-ray tube kVp may also affect heel effect. For example, x-ray intensity along chestwall to nipple direction drops more quickly at low kVp than at high kVp. In order to perfectly flatten x-ray images taken at different kVp, it is better to use a gain map taken at that kVp. Phantom thickness, and the presence of x-ray anti-scatter grid, can also modify the intensity profile of x-ray beam on detector that affects the system gain map.

Among the individual components 304-314, the detector pixel-to-pixel gain variations 304 can be the most dose-demanding task. The detector pixel-to-pixel gain component is a high-resolution component that requires high-dose exposures to reliably measure. Other individual components 306-314 may only include low-resolution components and therefore do not require high-dose exposures to measure. Rather, individual components 306-314 can be reliably measured using low-dose exposures.

The gain map 302 at each of the plurality of projection angles can be decomposed into a plurality of components, including high-resolution components and low-resolution components. However, the plurality of gain maps, each corresponding to a projection angle, share common components.

Among the disclosed individual components 304-314, the detector pixel-to-pixel variation map 304, filter map 306, kV map 310, grid map 312 and thickness map 314 have very minimal variation at the different projection angles. Only the view angle 308 includes significant variations based on the projection angle. As a result, in some examples, the detector pixel-to-pixel variation map 304, filter map 306, kV map 310, grid map 312 and thickness map 314 may be extracted once and shared between the different gain maps. However, since the view angle map 308 varies as the projection angle changes, the view angle map 308 may be extracted for each of the projection angles.

The final gain map may thus include a product of commonly shared angle-independent reference map, which includes the detector pixel-to-pixel variation map 304, filter map 306, kV map 310, grid map 312 and thickness map 314, and view angle map 308. By re-using gain map components that are common among the different projection angles, multiple high-dose exposures to measure gain maps at each projection can be avoided. The process of extraction high-dose and low-dose components from a gain map is further described in relation to FIG. 4.

A desirable commercial implementation may include a common reference map that includes high and low resolution components with the exception of the angle map, but in other implementations, the common reference map may include a combination of high and low resolution components with the exception one of: the filter map, kV map, grid map and thickness map.

FIG. 4 illustrates an example schematic representation of decomposition of a gain map into multi-scale components.

As described in relation to FIG. 3, a gain map may be viewed as a product of high-resolution and low-resolution component maps. A multi-scale decomposition process may be performed on an image to decompose the image into a detailed image and a residual image. The multi-scale decomposition process may be repeated several times on the resulting residual image to further extract the high-resolution components out of the image. At each level, the high-resolution components are extracted out to form the detailed image and leftover components of the image are used as the residual image from which the next level of decomposition is performed.

After several levels of decomposition, the resolution of the image becomes adequately low and there is no need to perform any more decomposition. The detailed images that are extracted out at the first few levels of decomposition are more sensitive to the high-dose components such as the detector pixel-to-pixel gain variation and less sensitive to low-dose components such as kV, filter, angle, grid and thickness. For example, the detailed images that include the high-resolution components may be used to generate a high-dose gain map that includes the detector pixel-to-pixel variation data. The residual images of the last few levels of decomposition are less sensitive to dose and includes data regarding the low-resolution components, such as kV, filter, angle, grid and thickness. For example, the residual images that include the low-resolution components may be used to generate a low-resolution gain map that includes the filter data, view angle data, kV data, grid data and thickness data.

An original image 402 may include an x-ray projection image of a phantom at one of the plurality of projection angles. The original image 402 may be decomposed into a detailed image 404 and a residual image 406. The process of decomposition may be done using a multi-scale pyramidal decomposition process, a wavelet decomposition process, an FFT decomposition process. Other types of decomposition processes are also possible.

The original image 402 may be decomposed into a first level detailed image 404 and a first level residual image 406 at a first level or level 1 of the decomposition process. The process may be repeated by decomposing the first level residual image 406 into a second level detailed image 408 and a second level residual image 410 for level 2 of the decomposition process. The decomposition process may continue as the second level residual image 410 is decomposed into a third level detailed image 412 and a third level residual image 414, the third level residual image 414 is decomposed into a fourth level detailed image 416 and a fourth level residual image 418 and the fourth level residual image 418 decomposed into a fifth level detailed image 420 and a fifth level residual image 422.

The decomposition process may continue until the image can no longer be decomposed or until sufficient number of decomposition cycles have been achieved to extract the high-resolution and low-resolution components. For example, the decomposition process may continue until a N-th level detailed image 424 and N-th residual image 426 are generated.

The low-dose x-ray projection images of the phantom acquired at the plurality of projection angles by the image acquisition module 204 (described above in relation to FIG. 2) is decomposed into multiple levels. The residual image from the last few levels of decomposition include low-resolution components that may be extracted for use in generating a final gain map as described in relation to gain map generation 208 of FIG. 2.

The level of the decomposed residual image from which a low-dose gain map is generated and low-resolution components are extracted may be selected based on an evaluation of whether enough of the high-resolution component of the residual image have been filtered out and whether the residual image includes enough resolution for extracting the low-resolution components. The most desirable level may be the third level to sixth level or last level of decomposition. The exact level of decomposition from which the low-resolution components are extracted may differ from image to image and between tomosynthesis processes.

The high-dose x-ray projection image that is constructed by combining the plurality of low-dose x-ray projection images of the phantom by the image acquisition module 204 is decomposed into multiple levels. The detailed images from the first few levels of decomposition include high-resolution components that may be extracted for use in generating a final gain map as described in relation to gain map generation 208 of FIG. 2.

In some examples, the high-resolution components may be extracted from a gain map generated from the first level detailed image 404. In other examples, the high-resolution components may be extracted from a gain map generated from a detailed image from another level other than the first level. The ideal level may be selected based on the level that provides the best high-resolution components.

FIG. 5 illustrates an example method 500 for gain calibration at a plurality of projection angles for a tomosynthesis sweep.

The method 500 begins with operation 502. In operation 502, the imaging system 100 is used to perform one or more tomosynthesis sweeps to acquire a plurality of tomosynthesis projection x-ray images of a phantom. The acquired plurality of images are low-dose x-ray projection images.

The image acquisition module 204 of the image correction engine 202 may be used to configure the acquisition of the plurality of images by the imaging system 100. A calibration phantom may be made of a uniform material with a substantially uniform thickness to simulate a patient's compressed breast. The phantom may be secured in the immobilizer unit 104 of the imaging system 100, in a position similar to that of a patient's breast when x-rays of a patient's breast are taken. To derive gain maps, the system 100 is operated in a tomosynthesis mode and an x-ray projection image of the phantom is taken at each of the plurality of imaging parameters. In some examples, the imaging parameters may include projection angles. In other examples, the imaging parameters may include kVp, filter material type, breast thickness, or grid position. Other types of imaging parameters are also possible. Each projection x-ray image is represented by of pixel values related to the x-rays received at respective pixel positions of an array of imaging pixels in receptor 116.

Operation 504 includes generating a high-dose x-ray image. The high-dose image generation module 206 of the image correction engine 202 may generate the high-dose x-ray image by combining and averaging the plurality of low-dose x-ray projection images that were acquired in operation 502. As further described in relation to FIG. 2, combining and averaging the low-dose images results in a high-dose image that reduces noise caused due the low photon counts.

Operation 506 includes generating a high-dose gain map from the high-dose x-ray image generated in operation 504. For example, generating a high-dose gain map may include determining a mean signal count for an array of pixels associated with the high-dose x-ray image. In addition to the determining a mean signal count, the generating a high-dose gain map includes determining a raw signal count for each of the pixels from the array of pixels associated with the high dose x-ray image.

The gain map may be generated by calculating the gain correction coefficient for each of the pixels in the array of pixels associated with the high-dose x-ray image and assembling the gain correction coefficient for each of the pixels in the array of pixels into the high-dose gain map. In some examples, the gain correction coefficient may be a product of the mean signal count and an inverse of the raw signal count for a particular pixel. In other examples, the gain correction coefficients may be calculated in a different way.

Operation 508 includes extracting high-resolution components from the high-dose gain map that was generated in operation 506. The gain map generation module 208 of the image correction engine 202 may use the decomposition process described in relation to FIG. 2 to decompose a high-dose gain map generated in operation 506 into multi-levels of components and extract the high-resolution components from the detailed image of the first or one of the first few levels of the decomposition process. In some examples, the high-resolution component may only include the detector pixel-to-pixel variation data. In other examples, the high-dose gain map may also include other types of both high-resolution and low-resolution data.

High-resolution components may not be extracted from a high-dose gain map generated from the high-dose projection image at all and operation 508 may be skipped. The high-dose gain map itself may be used instead of extracting individual components of the gain map. When the high-resolution component of the high-dose gain map in the disclosed example consists only or mostly the detector pixel-to-pixel variation data, the step of extracting the high-resolution components from the high-dose gain map may be unnecessary and the high-dose gain map itself may be used in the calculation of the final gain map. As such, the high-dose gain map may not need to be extracted and operation 508 may be skipped and operation 510 may be performed upon completion of operation 506.

Operation 510 includes generating a plurality of low-dose gain maps, where each of the plurality of low-dose gain maps is associated with one of the plurality of projection x-ray images corresponding to one of the plurality of imaging parameters. The gain map generation module 208 of the image correction engine 202 may generate a gain map for each of the plurality of imaging parameters of the tomosynthesis scan based on the corresponding x-ray projection image acquired for that imaging parameter from operation 502.

The process of generating a low-dose gain map may be the same or similar to the process used in generating the high-dose gain map in operation 506. One difference in the process may be that the gain map is generated from a low-dose x-ray projection image acquired in operation 502 rather than the high-dose projection image generated in operation 504.

Operation 512 includes extracting low-resolution components from each of the plurality of low-dose gain maps generated in operation 510. The gain map generation module 208 of the image correction engine 202 may use the decomposition process described in relation to FIG. 2 to decompose a low-dose gain map generated in operation 510 into multi-levels of components and extract the low-resolution components from the detailed image of the last or one of the last few levels of the decomposition process.

The low-resolution components may include a filter data, view angle data, kV data, grid data and thickness data. The low-dose gain map may also include other types of low-resolution data.

In most cases, high-resolution components of low dose gain map are not used at all in any step of final gain map generation since only the low-resolution components of low dose gain map are included and combined with high dose gain map or its high-resolution components. Therefore the decomposition process for low dose gain is frequently simplified as to skipping a full decomposition process to convert low dose gain map into each of its high- and low-resolution level components, and going directly to the N-th level low resolution residual component image. In such cases, more efficient processing algorithm other than full multi-scale deposition process can be selected to perform the calculation. For example, a 2×2, 4×4, 8×8, (and so on) pixel binning method may be used to derive the low-resolution component of low dose gain map.

Operation 514 includes combining the high-resolution component of the high-dose gain map with each of the plurality of low-resolution components extracted from each of the low-dose gain maps to generate a final gain map for each of the plurality of imaging parameters. The gain map generation module 208 of the image correction engine 202 may generate a final gain map by combining the high-dose gain map or the high-resolution component of the high-dose gain map with the low-resolution components of the low-dose gain map acquired and generated in operations 502-512.

As further described in relation to FIG. 3, the high-dose gain map or the high-resolution component of the high-dose gain map comprises the detector pixel-to-pixel variations. Typically, when the imaging parameter includes the projection angle, the detector pixel-to-pixel variations do not change at different projection angles. Most of the low-resolution components of the low-dose gain maps also do not change at different projection angles except for the angle component.

The high-resolution components and low-resolution components that do not change between the different imaging parameters may be extracted out and a common reference gain map is generated. The remaining component or components of the low-dose gain map that differs between each of the imaging parameters may then be separately combined with the common reference gain map at each of the imaging parameters to generate a final gain map at each of the imaging parameters. In some examples, the imaging parameter dependent component may be the view angle map. In other examples, the imaging parameter dependent component may be the filter map, kV map, grid map or thickness map. Other options are also possible.

Figure 6:
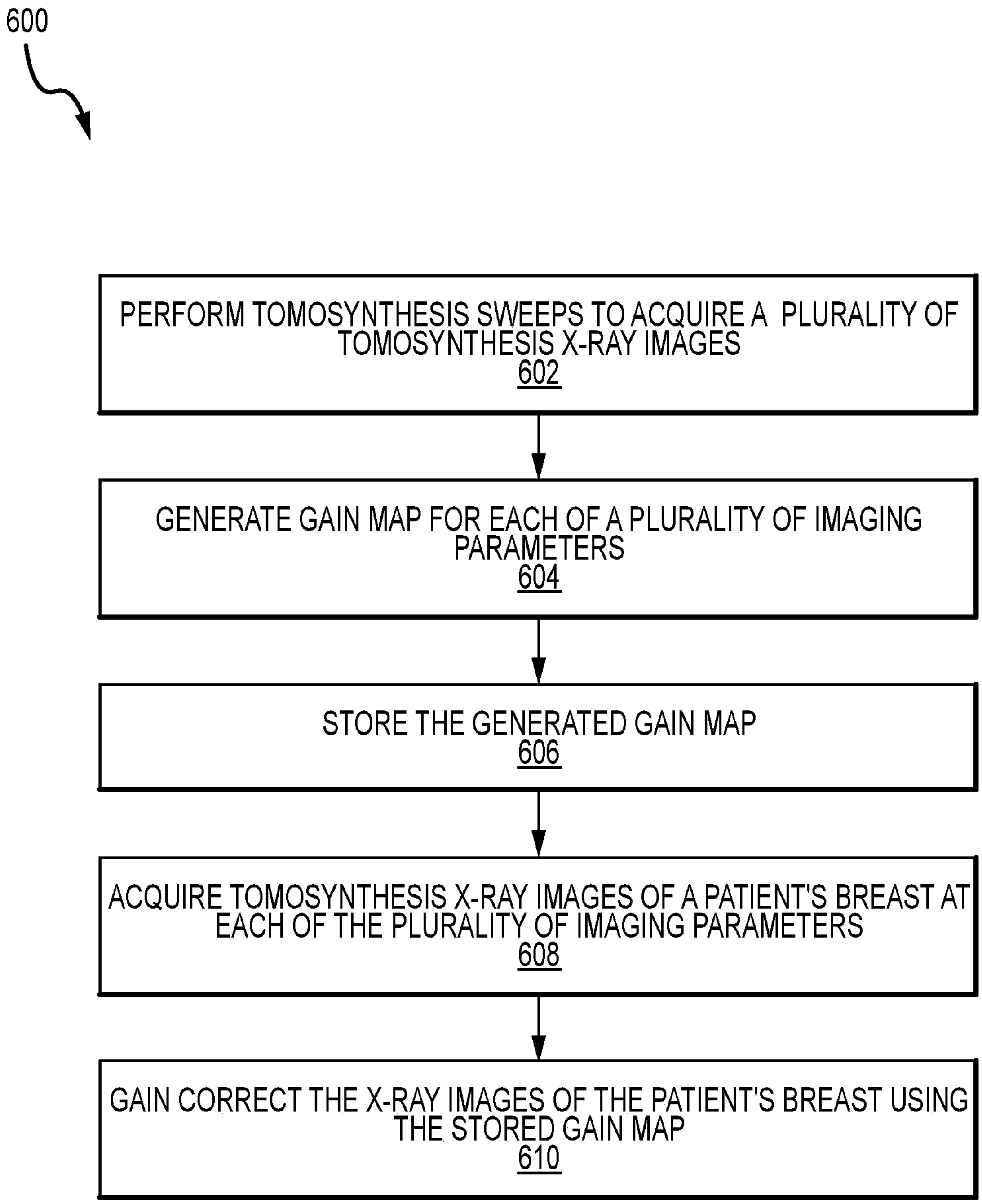
FIG. 6 illustrates an example method for image correction to compensate for gain offsets in a tomosynthesis process.

FIG. 6 illustrates an example method 600 for image correction to compensate for gain offsets in a tomosynthesis process.

The method 600 begins with operation 602. In operation 602, the imaging system 100 is used to perform one or more tomosynthesis sweeps to acquire a plurality of tomosynthesis projection x-ray images of a phantom, as described in relation to operation 502 of FIG. 5.

In operation 604, a gain map for each of the plurality of imaging parameters is generated from the x-ray projection images of the phantom that were acquired in operation 602. The process to normalize the image detector output among different pixels is called "gain correction." The gain map is a map of gain correction coefficients associated with each pixel in the array of imaging pixels of the image receptor 116. The process of generating the gain map is described in greater detail in relation to FIGS. 2-5.

In operation 606, the generated gain map from operation 604 is stored. In some examples, the generated gain map may be stored in the imaging system 100 itself. In other examples, the generated gain map may be stored in a remote location accessible via a network and may be retrieved as required.

Although the disclosed systems and methods describe generation of gain maps and image correction processes with respect to a calibration phantom, it is to be noted that different types of calibration phantoms may be used to simulate different breast imaging protocols and a plurality of gain maps associated with a plurality of breast imaging protocols may be generated and stored. The appropriate set of gain maps can be automatically retrieved and used upon the selection of a tomosynthesis breast imaging protocol.

In operation 608, tomosynthesis x-ray images of a patient's breast at each of the plurality of imaging parameters is acquired. To acquire projection images of the patient, the phantom may be removed, and a patient's breast may be secured in immobilizer unit 104 is x-rayed using tomosynthesis imaging sequences. In an example where the imaging parameter is the projection angles, the tomosynthesis imaging sequence of a patient's breast may generate projection x-ray images taken at a plurality of projection angles that may or may not be the same in number and angle values as the projection angles used in acquiring phantom images.

In operation 610, the x-ray images of the patient's breast are gain corrected using the stored gain map from operation 606. The system control and workstation unit 138 of the imaging system 100 may comprise processing equipment that receives from the image receptor 116, the projection images of the phantom and the projection images of the patient's breast from operations 602 and 608. The workstation unit 138 may then carry out gain-correcting processes on the breast images using the gain maps that were generated and stored in operations 604 and 606.

The workstation unit 138 may also cause the displaying of the resulting gain-corrected images, storing of the images and other information, providing system control to control aspects of the gain-corrected images. The workstation unit 138 may also be used to identify suspected abnormalities or select other characteristics, prepare or control images for display, prepare images for storage such as DICOM-compliant storage, provide an interface for an x-ray technologist or other health professional, and provide other control functions associated with the images.

Figure 7:
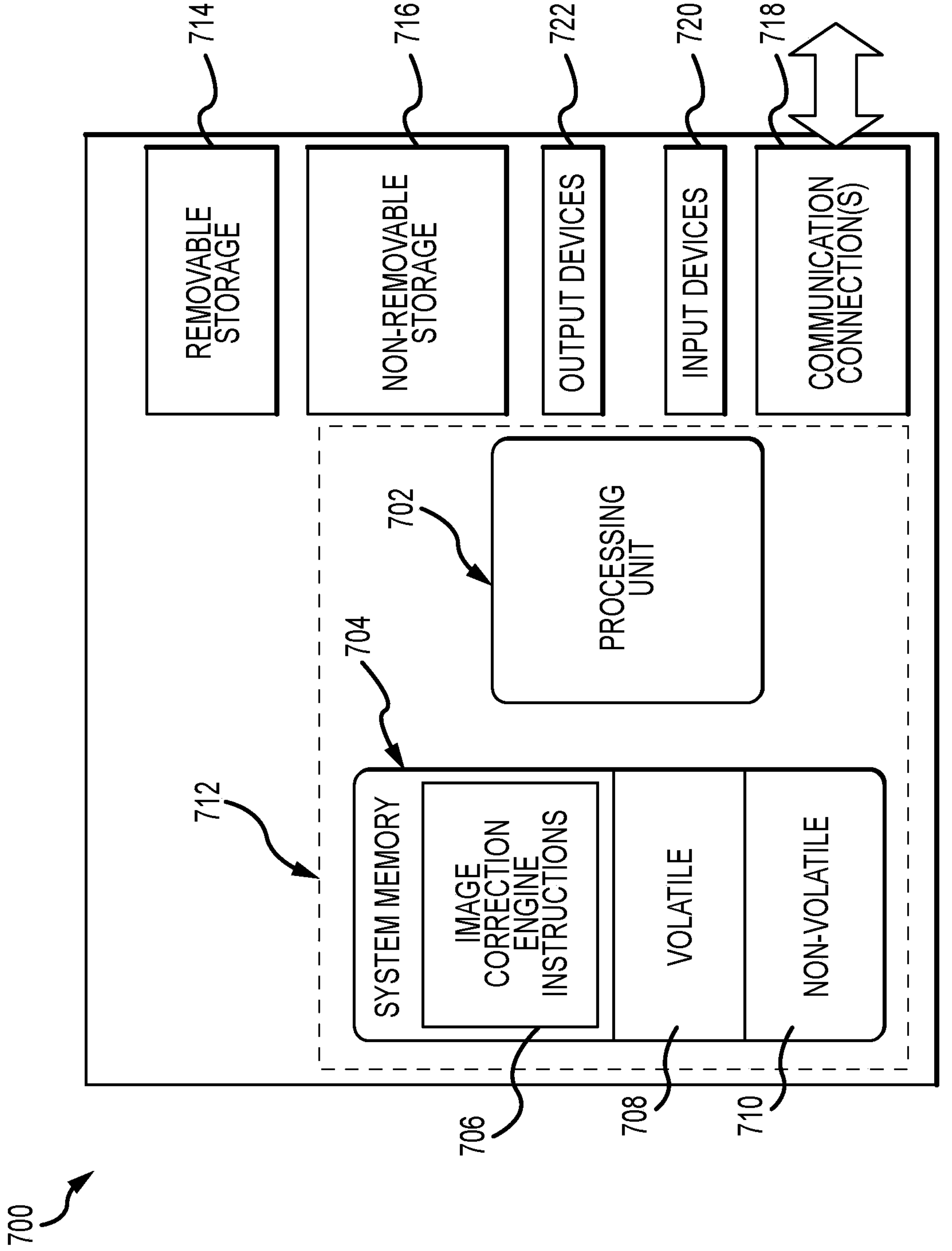
FIG. 7 depicts an example of a suitable operating environment in which one or more of the present examples can be implemented.

FIG. 7 illustrates one example of a suitable operating environment 700 in which one or more of the present examples can be implemented. This operating environment may be incorporated directly into the visualization systems disclosed herein, or may be incorporated into a computer system discrete from, but used to control the breast imaging systems described herein, such as computer system may be, e.g., the workstation depicted in FIG. 1A. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 700 typically includes at least one processing unit 702 and memory 704. Depending on the exact configuration and type of computing device, memory 704, storing, among other things, instructions 706 (to read from data storage devices or sensors, or perform other methods disclosed herein) can be volatile 708 (such as RAM), non-volatile 710 (such as ROM, flash memory, etc.), or some combination of the two. The instructions 706 may include image correction engine instructions that when executed by the processing unit 702 cause the processing unit 702 to cause the image correction engine 202 to perform the operations described in further in relation to FIG. 2. This most basic configuration is illustrated in FIG. 7 by dashed line 712. Further, environment 700 can also include storage devices (removable, 714, and/or non-removable, 716) including, but not limited to, magnetic or optical disks or tape. Similarly, environment 700 can also have input device(s) 720 such as touch screens, keyboard, mouse, pen, voice input, etc., and/or output device(s) 722 such as a display, speakers, printer, etc. Also included in the environment can be one or more communication connections 718, such as LAN, WAN, point to point, Bluetooth, RF, etc.

Operating environment 700 typically includes at least some form of computer readable media. Computer readable media can be any available media that can be accessed by processing unit 702 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 700 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein include such modules or instructions executable by computer system 700 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 700 is part of a network that stores data in remote storage media for use by the computer system 700.

Figure 8:
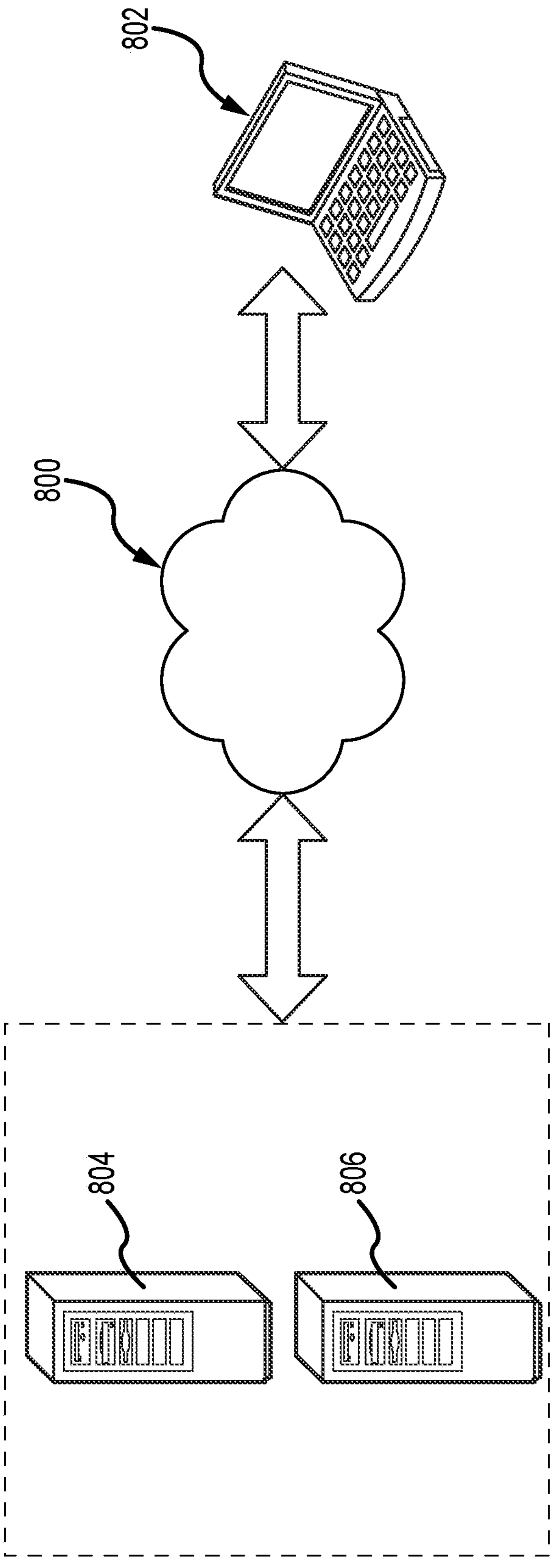
FIG. 8 depicts an example of a network in which the various systems and methods disclosed herein may operate.

FIG. 8 is an embodiment of a network 800 in which the various systems and methods disclosed herein may operate. In embodiments, a client device, such as client device 802, may communicate with one or more servers, such as servers 804 and 806, via a network 800. In embodiments, a client device may be a standalone imaging system (e.g., imaging system 100 depicted in FIG. 1A) that includes all the functionality described herein. The client device may also include or incorporate a laptop, a personal computer, a smart phone, a PDA, a netbook, or any other type of computing device, such as the computing device in FIG. 7. In examples, such a client device may be connected to an imaging system. In embodiments, servers 804 and 806 may also be any type of computing device, such as the computing device illustrated in FIG. 7. Network 800 may be any type of network capable of facilitating communications between the client device and one or more servers 804 and 806. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 804 may be employed to perform the systems and methods disclosed herein, such as the methods for imaging discussed herein. Client device 802 may interact with server 804 via network 800. In further embodiments, the client device 802 may also perform functionality disclosed herein, such as scanning and image processing, which can then be provided to servers 804 and/or 806.

Illustrative examples of the systems and methods described herein are provided below. An embodiment of the system or method described herein may include any one or more, and any combination of, the clauses described below:

Clause 1. A method for gain calibration at a plurality of imaging parameters for a tomosynthesis sweep, the method comprising: performing one or more tomosynthesis sweeps to acquire a plurality of tomosynthesis projection x-ray images, each of the plurality of tomosynthesis projection x-ray images associated with one of the plurality of imaging parameters; generating a high-dose x-ray image by averaging the plurality of tomosynthesis projection x-ray images; generating a high-dose gain map associated with the high-dose x-ray image; generating a plurality of low-dose gain maps, each of the plurality of low-dose gain maps associated with one of the plurality of tomosynthesis projection x-ray images associated with one of the plurality of imaging parameters; decomposing each of the plurality of low-dose gain maps into a plurality of component levels; extracting low-resolution components from the plurality of component levels for each of the plurality of low-dose gain maps; and for each of the plurality of imaging parameters, combining the high-dose gain map with the each of the low-resolution components of the low-dose gain maps to generate a final gain map for each of the plurality of imaging parameters.

Clause 2. The method of clause 1, further comprising: storing the final gain map for each of the plurality of imaging parameters; acquiring tomosynthesis x-ray images of a patient's breast at each of the plurality of imaging parameters; and gain correcting the tomosynthesis x-ray images of the patient's breast using the stored final gain map for each of the plurality of imaging parameters to produce gain-corrected breast images.

Clause 3. The method of any of clauses 1-2, wherein the imaging parameters includes one of: projection angle, kVp, filter material type, breast thickness and grid position.

Clause 4. The method of any of clauses 1-3, wherein the one or more tomosynthesis sweeps are performed by an image acquisition unit comprising an x-ray source and an x-ray image receptor, wherein the image acquisition unit acquires projection x-ray images of an object at the plurality of imaging parameters.

Clause 5. The method of any of clauses 1-4, wherein generating the high-dose gain map comprises: determining a mean signal count for an array of pixels associated with the high-dose x-ray image; determining a raw signal count for each of the pixels from the array of pixels associated with the high-dose x-ray image; calculating the gain correction coefficient for each of the pixels in the array of pixels associated with the high-dose x-ray image, wherein the gain correction coefficient is a product of the mean signal count and an inverse of the raw signal count for the particular pixel; and assembling the gain correction coefficient for each of the pixels in the array of pixels into the high-dose gain map.

Clause 6. The method of any of clauses 1-5, wherein decomposing each of the plurality of low-dose gain maps includes decomposing into a plurality of resolution levels, wherein each level of the plurality of resolution levels includes a detail image and a residual image.

Clause 7. The method of clause 6, wherein decomposing each of the plurality of low-dose gain maps is performed using a multi-scale decomposition process.

Clause 8. The method of any of clauses 6-7, wherein extracting the low-resolution components includes extracting low-resolution components from the residual image of a last level of the plurality of resolution levels.

Clause 9. The method of any of clauses 1-8, wherein the high-dose gain map comprises x-ray detector pixel-to-pixel gain variation data.

Clause 10. The method of any of clauses 1-9, wherein the low-resolution components comprise one of: an angle data, a kV data, a filter data, a grid data, and a thickness data.

Clause 11. A tomosynthesis imaging system for gain calibration at a plurality of projection angles, the system comprising: an image acquisition unit comprising an x-ray source and an x-ray image receptor, wherein the image acquisition unit acquires projection x-ray images of an object at the plurality of projection angles; a processor; memory including instructions that when executed by the processor cause the processor to: perform one or more tomosynthesis sweeps to acquire a plurality of tomosynthesis projection x-ray images, each of the plurality of tomosynthesis projection x-ray images associated with one of the plurality of projection angles; generate a high-dose x-ray image by averaging the plurality of tomosynthesis projection x-ray images; generate a high-dose gain map associated with the high-dose x-ray image; decompose the high-dose gain map into a first plurality of component levels; extract a high-resolution component from the first plurality of component levels; generate a plurality of low-dose gain maps, each of the plurality of low-dose gain maps associated with one of the plurality of tomosynthesis projection x-ray images associated with one of the plurality of projection angles; decompose each of the plurality of low-dose gain maps into a second plurality of component levels; extract low-resolution components from each of the plurality of low-dose gain maps, wherein the low-resolution components comprise an angle map; and for each of the plurality of projection angles, combine the high-resolution component of the high-dose gain map with the each of the low-resolution components of the low-dose gain maps to generate a final gain map for each of the plurality of projection angles.

Clause 12. The system of clause 11, wherein the instructions when executed by the processor further cause the processor to: store the final gain map for each of the plurality of projection angles; acquire tomosynthesis x-ray images of a patient's breast at each of the plurality of projection angles; and gain correct the tomosynthesis x-ray images of the patient's breast using the stored final gain map for each of the plurality of projection angles to produce gain-corrected breast images.

Clause 13. The system of any of clauses 11-12, wherein the one or more tomosynthesis sweeps are performed to acquire a plurality of tomosynthesis projection x-ray images of a phantom.

Clause 14. The system of any of clauses 11-13, wherein the instructions when executed by the processor to generate the high-dose gain map cause the processor to: determine a mean signal count for an array of pixels associated with the high-dose x-ray image; determine a raw signal count for each of the pixels from the array of pixels associated with the high-dose x-ray image; calculate the gain correction coefficient for each of the pixels in the array of pixels associated with the high-dose x-ray image, wherein the gain correction coefficient is a product of the mean signal count and an inverse of the raw signal count for the particular pixel; and assemble the gain correction coefficient for each of the pixels in the array of pixels into the high-dose gain map.

Clause 15. The system of any of clauses 11-14, wherein decomposing the high-dose gain map and decomposing each of the plurality of low-dose gain maps includes decomposing into a plurality of resolution levels, wherein each level of the plurality of resolution levels includes a detail image and a residual image.

Clause 16. The system of clause 15, wherein decomposing the high-dose gain map and decomposing each of the plurality of low-dose gain maps is performed using a multi-scale decomposition process.

Clause 17. The system of any of clauses 15-16, wherein extracting the high-resolution component includes extracting a high-resolution component from the detail image of a level above a last level of the plurality of resolution levels and extracting the low-resolution components includes extracting low-resolution components from the residual image of a last level of the plurality of resolution levels.

Clause 18. The system of any of clauses 11-17, wherein the high-resolution component comprises x-ray detector pixel-to-pixel gain variation data.

Clause 19. The system of any of clauses 11-18, wherein the low-resolution components further comprise one of an angle data, a kV data, a filter data, a grid data, and a thickness data.

Clause 20. A method for gain calibration at a plurality of projection angles for a tomosynthesis sweep, the method comprising: performing one or more tomosynthesis sweeps to acquire a plurality of tomosynthesis projection x-ray images, each of the plurality of tomosynthesis projection x-ray images associated with one of the plurality of projection angles; generating a high-dose x-ray image by averaging the plurality of tomosynthesis projection x-ray images; generating a high-dose gain map associated with the high-dose x-ray image; decomposing the high-dose gain map into a first plurality of component levels; extracting a high-resolution component from the first plurality of component levels; generating a plurality of low-dose gain maps, each of the plurality of low-dose gain maps associated with one of the plurality of tomosynthesis projection x-ray images associated with one of the plurality of projection angles; decomposing each of the plurality of low-dose gain maps into a second plurality of component levels; extracting low-resolution components from each of the plurality of low-dose gain maps, wherein the low-resolution components comprise an angle map; and for each of the plurality of projection angles, combining the high-resolution component with the each of the low-resolution components to generate a final gain map for each of the plurality of projection angles.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of imaging a breast of a patient at an imaging system including an x-ray source and an x-ray detector, the method comprising:

immobilizing, via an immobilizer unit, the breast;

acquiring a plurality of tomosynthesis projection images of the breast at different projection angles via the x-ray source and the x-ray detector;

gain correcting the plurality of tomosynthesis projection images via calibrated gain maps for each projection angle of the plurality of tomosynthesis projection images, wherein the calibrated gain maps are based on a high-dose gain map associated with a high-dose x-ray image averaged over a plurality of projection angles during calibration and a plurality of low-dose gain maps associated with each projection angle during calibration, wherein the plurality of low-dose gain maps are decomposed and low-resolution components are extracted such that the calibrated gain maps combine the high-dose gain map with each of the low-resolution components of the plurality of low-dose gain maps of the different projection angles; and displaying one or more images of the breast based on the gain corrected plurality of tomosynthesis projection images.

2. The method of claim 1, further comprising retrieving the calibrated gain maps stored locally at the imaging system.

3. The method of claim 1, further comprising receiving the calibrated gain maps remotely stored from the imaging system.

4. The method of claim 1, further comprising retrieving the calibrated gain maps associated with a tomosynthesis breast imaging protocol used to acquire the plurality of tomosynthesis projection images of the breast.

5. The method of claim 1, further comprising calibrating the calibrated gain maps prior to imaging the breast of the patient, wherein calibrating the calibrated gain maps comprises:

immobilizing, via the immobilizer unit, a phantom;

acquiring a plurality of tomosynthesis projection images of the phantom at different projection angles via the x-ray source and the x-ray detector; and generating the calibrated gain maps based on the acquired plurality of tomosynthesis projection images of the phantom.

6. The method of claim 5, wherein generating the calibrated gain maps comprises:

generating the high-dose x-ray image by averaging the acquired plurality of tomosynthesis projection images of the phantom;

generating the high-dose gain map associated with the high-dose x-ray image;

generating the plurality of low-dose gain maps, each of the plurality of low-dose gain maps associated with one of the acquired plurality of tomosynthesis projection x-ray images of the phantom;

decomposing each of the plurality of low-dose gain maps into at least one component level;

extracting the low-resolution components from the at least one component level for each of the plurality of low-dose gain maps;

combining the high-dose gain map with the each of the low-resolution components of the low-dose gain maps to generate the calibrated gain maps; and saving the calibrated gain maps.

7. The method of claim 6, wherein the at least one component level includes a plurality of component levels.

8. The method of claim 6, wherein generating the calibrated gain maps further comprise extracting high-resolution components from the high-dose gain map.

9. The method of claim 1, wherein the low-resolution components comprise one of: an angle data, a kV data, a filter data, a grid data, and a thickness data.

10. The method of claim 1, further comprising identifying suspected abnormalities from the displayed one or more images of the breast that are based on the gain corrected plurality of tomosynthesis projection images.

11. A tomosynthesis imaging system comprising:

an image acquisition unit including an x-ray source and an x-ray detector configured to acquire tomosynthesis projection images;

an immobilizer unit configured to immobilize a breast of a patient;

a display;

a processor; and memory storing calibrated gain maps and including instructions that when executed by the processor cause the processor to:

acquire a plurality of tomosynthesis projection images of the breast immobilized at the immobilizer unit at different projection angles;

gain correct the plurality of tomosynthesis projection images via the calibrated gain maps for each projection angle of the plurality of tomosynthesis projection images, wherein the calibrated gain maps are based on a high-dose gain map associated with a high-dose x-ray image averaged over a plurality of projection angles during calibration and a plurality of low-dose gain maps associated with each projection angle during calibration, wherein the plurality of low-dose gain maps are decomposed and low-resolution components are extracted such that the calibrated gain maps combine the high-dose gain map with each of the low-resolution components of the plurality of low-dose gain maps of the different projection angles; and display one or more images of the breast based on the gain corrected plurality of tomosynthesis projection images.

12. The tomosynthesis imaging system of claim 11, wherein the instructions when executed by the processor further cause the processor to retrieve the calibrated gain maps stored locally at the imaging system.

13. The tomosynthesis imaging system of claim 11, wherein the instructions when executed by the processor further cause the processor to receive the calibrated gain maps remotely stored from the imaging system.

14. The tomosynthesis imaging system of claim 11, wherein the instructions when executed by the processor further cause the processor to retrieve the calibrated gain maps associated with a tomosynthesis breast imaging protocol used to acquire the plurality of tomosynthesis projection images of the breast.

15. The tomosynthesis imaging system of claim 11, wherein the instructions when executed by the processor further cause the processor to calibrate the calibrated gain maps prior to imaging the breast of the patient, wherein calibration of the calibrated gain maps comprises:

acquire a plurality of tomosynthesis projection images of a phantom immobilized at the immobilizer unit at different projection angles; and generate the calibrated gain maps based on the acquired plurality of tomosynthesis projection images of the phantom.

16. The tomosynthesis imaging system of claim 15, wherein the instructions when executed by the processor further cause the processor to generate the calibrated gain maps via:

generate the high-dose x-ray image by averaging the acquired plurality of tomosynthesis projection images of the phantom;

generate the high-dose gain map associated with the high-dose x-ray image;

generate the plurality of low-dose gain maps, each of the plurality of low-dose gain maps associated with one of the acquired plurality of tomosynthesis projection x-ray images of the phantom;

decompose each of the plurality of low-dose gain maps into at least one component level;

extract the low-resolution components from the at least one component level for each of the plurality of low-dose gain maps;

combine the high-dose gain map with the each of the low-resolution components of the low-dose gain maps to generate the calibrated gain maps; and save the calibrated gain maps.

17. The tomosynthesis imaging system of claim 16, wherein the at least one component level includes a plurality of component levels.

18. The tomosynthesis imaging system of claim 16, wherein the instructions when executed by the processor further cause the processor to extract high-resolution components from the high-dose gain map to generate the calibrated gain maps.

19. The tomosynthesis imaging system of claim 11, wherein the low-resolution components comprise one of: an angle data, a kV data, a filter data, a grid data, and a thickness data.

20. The tomosynthesis imaging system of claim 11, wherein the instructions when executed by the processor further cause the processor to identify suspected abnormalities from the displayed one or more images of the breast that are based on the gain corrected plurality of tomosynthesis projection images.

* * * * *